US012661287B1

(12) United States Patent
Murray

(10) Patent No.: US 12,661,287 B1
(45) Date of Patent: Jun. 23, 2026

(54) BEDSIDE ATTACHMENT DEVICE FOR HOSPITAL BEDS

(71) Applicant: Troy M. Murray, Columbia, MD (US)

(72) Inventor: Troy M. Murray, Columbia, MD (US)

( * ) Notice: Subject to any disclaimer, the term of this patent is extended or adjusted under 35 U.S.C. 154(b) by 0 days.

(21) Appl. No.: 19/533,838

(22) Filed: Feb. 9, 2026

(51) Int. Cl.
| | |
|---|---|
| *A61G 7/05* | (2006.01) |
| *A47C 21/00* | (2006.01) |
| *A61B 5/00* | (2006.01) |
| *H04M 1/04* | (2006.01) |

(52) U.S. Cl.
CPC ........... *A61G 7/0524* (2016.11); *A47C 21/00* (2013.01); *A61B 5/7465* (2013.01); *A61G 7/0503* (2013.01); *A47C 21/003* (2013.01); *A61G 7/0507* (2013.01); *H04M 1/04* (2013.01)

(58) Field of Classification Search
CPC .. A61G 7/0524; A61G 7/0507; A61G 7/0503; A61B 5/7465; A47C 21/00; A47C 21/003; A47B 23/025; A47B 23/02; H04M 1/04
USPC ............................... 5/503.1, 507.1, 658, 663
See application file for complete search history.

(56) References Cited

U.S. PATENT DOCUMENTS

| | | | | | |
|---|---|---|---|---|---|
| 3,967,666 | A | * | 7/1976 | Farrar ................... | A61G 7/0503 |
| | | | | | 383/7 |
| 4,357,881 | A | * | 11/1982 | De Long ................ | A47B 23/02 |
| | | | | | 211/88.01 |
| 4,484,367 | A | * | 11/1984 | Jenkins ................ | A61G 7/0524 |
| | | | | | 5/503.1 |

| | | | | | |
|---|---|---|---|---|---|
| 4,504,992 | A | * | 3/1985 | Herron ..................... | H04M 1/11 |
| | | | | | 379/454 |
| 4,945,561 | A | * | 7/1990 | Rioux, Jr. ............... | H04M 1/04 |
| | | | | | 379/454 |
| 4,998,277 | A | * | 3/1991 | Rioux, Jr. ............... | H04M 1/04 |
| | | | | | 5/503.1 |
| 4,998,700 | A | * | 3/1991 | McKaig ................. | A47C 21/00 |
| | | | | | 5/503.1 |
| 5,222,132 | A | * | 6/1993 | Rioux, Jr. ............ | A47B 23/025 |
| | | | | | 379/454 |
| 5,365,623 | A | * | 11/1994 | Springer .............. | A47C 21/003 |
| | | | | | 5/503.1 |
| 5,370,246 | A | * | 12/1994 | Traynor ............... | A61G 7/0503 |
| | | | | | 5/503.1 |
| 5,651,152 | A | * | 7/1997 | Ritchie .................... | A61G 7/05 |
| | | | | | 5/663 |

(Continued)

*Primary Examiner* — Robert G Santos
(74) *Attorney, Agent, or Firm* — Whiteford, Taylor & Preston, LLP; Peter J. Davis

(57) ABSTRACT

A bedside attachment device for hospital beds comprises a mounting system configured for tool-less, removable attachment to a hospital bed rail without permanent mounting hardware. The device supports at least three patient-accessible compartments including a phone compartment having a cable-routing feature, a nurse-call handset compartment having a retention feature, and a beverage holder movable between a deployed position for supporting a beverage container and a stowed position providing a reduced profile. When mounted to the bed rail, the device is configured to avoid interference with movement of the bed rail between raised and lowered positions, and in some embodiments the reduced profile enables the device to fit between a lowered bed rail and a mattress. The device may include a rail-engaging friction surface and may comprise wipeable, hospital-compatible materials with optional antibacterial additives.

20 Claims, 10 Drawing Sheets

(56) References Cited

U.S. PATENT DOCUMENTS

| | | | | |
|---|---|---|---|---|
| 6,253,399 | B1 * | 7/2001 | Wagner ................ | A47B 23/025 |
| | | | | 5/503.1 |
| 9,095,222 | B2 * | 8/2015 | Asaf .................... | A61G 7/0522 |
| 9,687,402 | B2 * | 6/2017 | Ellis .................... | A61G 7/0503 |
| 11,589,674 | B2 * | 2/2023 | Culveyhouse ....... | A47B 23/025 |
| 11,871,850 | B1 * | 1/2024 | Fang ................... | A47B 23/025 |
| 12,290,179 | B2 * | 5/2025 | Fang .................... | A47C 21/08 |
| 2013/0305451 | A1 * | 11/2013 | Asaf .................... | A61G 7/0522 |
| | | | | 5/503.1 |
| 2016/0324708 | A1 * | 11/2016 | Ellis .................... | A61G 7/0507 |
| 2021/0059400 | A1 * | 3/2021 | Culveyhouse ....... | A47B 23/025 |
| 2025/0024958 | A1 * | 1/2025 | Fang ................... | A61G 7/0524 |

* cited by examiner

BEDSIDE ATTACHMENT DEVICE FOR HOSPITAL BEDS

FIELD OF THE INVENTION

The present invention relates generally to bedside organizers and storage devices, and more particularly to a multi-compartment attachment device configured for tool-less mounting to hospital bed rails to provide organized storage for patient essential items including mobile phones, nurse-call handsets, and beverages.

BACKGROUND OF THE INVENTION

Hospital patients confined to beds face significant challenges in accessing and organizing essential personal items. Mobile phones, nurse-call handsets, beverage containers, and other necessities are typically scattered across bedside tables, windowsills, or loose on the bed itself. This disorganization creates multiple problems: items fall behind furniture becoming inaccessible, nurse-call devices are out of reach during emergencies, beverages spill causing patient discomfort and damage to equipment, and charging cables create tangled hazards.

The problem intensifies because hospital beds are dynamic environments. Bed rails move during patient repositioning, beds are raised and lowered, and rails are adjusted for patient safety. Any bedside storage solution must accommodate this constant motion without interfering with bed functionality or requiring permanent installation that damages hospital equipment. Additionally, when bed rails are lowered, any attached device must maintain a sufficiently low profile to fit between the bed rail and mattress without causing interference or requiring removal.

Existing solutions are inadequate. Generic bedside caddies designed for home use lack the specific compartments needed for hospital equipment, such as nurse-call handsets. Single-purpose holders for phones or cups exist but require patients to manage multiple separate devices. Many existing products require tools for installation, use permanent mounting hardware that damages bed rails, or interfere with the bed's range of motion. Furthermore, existing products often fail to meet hospital infection control standards, featuring porous materials, crevices that harbor bacteria, or surfaces that cannot withstand repeated cleaning with hospital-grade disinfectants.

Hospital staff have resorted to makeshift solutions such as taping items to bed rails or using plastic bags hung from rails, but these approaches are unsanitary, unprofessional in appearance, and fail to provide secure, organized storage. Patients and their families frequently express frustration with the lack of proper bedside organization in healthcare facilities.

There exists a need in the art for a bedside attachment device specifically designed for hospital environments that provides dedicated, organized storage for the specific items hospital patients need most: mobile phones with charging capability, nurse-call handsets, and beverage containers. Such an attachment device should install without tools, preserve full bed rail motion, maintain a low profile compatible with lowered bed rail positions, withstand hospital cleaning protocols, and provide an organized solution that enhances patient safety and comfort.

SUMMARY OF THE INVENTION

In accordance with certain aspects of an embodiment of the invention, a bedside attachment device is provided that is specifically configured for hospital bed environments. The device features a unique three-compartment configuration that provides dedicated storage for a mobile phone, a nurse-call handset, and a beverage container, all integrated into a mounting system that attaches to hospital bed rails without tools or permanent hardware.

In one aspect, the invention comprises a bedside attachment device for hospital beds including a mounting system configured for tool-less attachment to a hospital bed rail, wherein the mounting system comprises an inverted U-shaped bracket having a first inner face and a second outer face spaced apart to receive a bed rail therebetween, and wherein the mounting system preserves full range of motion of the bed rail. The device further includes three dedicated compartments mounted directly to the first inner face in fixed spatial relationship. The three dedicated compartments comprise: (i) a phone cradle compartment configured to receive a mobile phone and including a pass-through opening for routing a charging cable, (ii) a nurse-call handset slot compartment configured to receive a nurse-call handset, and (iii) a bottle holder compartment including a foldable bottle holder configured to transition between a deployed position for holding a beverage container and a stowed position against the first inner face.

The first inner face has a height dimension greater than the second outer face. The first inner face faces toward the patient when mounted on a bed rail and supports all three compartments. The second outer face faces away from the patient and has a height dimension sufficient to overlap and engage the outer side of the bed rail, maintaining stable attachment.

The three dedicated compartments are sized such that when the bottle holder is in the stowed position, the compartments maintain a low profile enabling the device to fit between the bed rail and the bed mattress when the bed rail is lowered into its down position. This feature allows the device to remain attached during bed rail articulation without interfering with bed operation or requiring removal.

The foldable bottle holder comprises a base panel pivotably mounted to the first inner face via first hinge brackets, wherein the base panel rotates between a vertical stowed position and a horizontal deployed position. The foldable bottle holder further comprises an upper holding bracket pivotably mounted to the first inner face via second hinge brackets positioned above the first hinge brackets, wherein the upper holding bracket comprises arc arms configured to extend around an upper portion of a beverage container in the deployed position.

Each of the three dedicated compartments is a standalone compartment structure independently mounted to the first inner face of the mounting system, rather than being contained within a separate housing structure. This direct-mount configuration simplifies construction, reduces weight, and maintains the low profile necessary for compatibility with lowered bed rails.

The mounting system is universally configurable for selective attachment to either a left or right hospital bed arm, enabling user-preferred orientation of the compartments. The device is constructed from hospital-grade materials with smooth, wipeable surfaces compatible with repeated cleaning with hospital disinfectants.

In another aspect, the invention provides a method of organizing patient essential items at a hospital bedside, comprising: providing a multi-compartment organizer having dedicated storage spaces for a mobile phone, a nurse-call handset, and a beverage container; attaching the organizer to a hospital bed rail without tools by positioning an inverted U-shaped mounting bracket over the rail; storing a mobile phone in a first compartment with a charging cable routed through a pass-through opening; storing a nurse-call handset in a second compartment separate from the mobile phone; and deploying a foldable bottle holder from a stowed position to hold a beverage container.

In yet another aspect, the invention provides a hospital bed accessory system comprising an attachment device with integrated storage for communication devices and beverage containers, wherein the attachment device is specifically adapted for the hospital environment through use of anti-bacterial materials, smooth wipeable surfaces, a low-profile design compatible with bed rail articulation, and a mounting system that preserves medical equipment functionality.

The invention may provide one or more of the following advantages over the prior art. The specific three-compart-ment configuration addresses the exact items hospital patients need most, with dedicated spaces preventing items from becoming disorganized or falling. The nurse-call hand-set slot ensures this critical safety device remains accessible at all times. The foldable bottle holder deploys when needed but stows flat to minimize space consumption and enable compatibility with lowered bed rails. The inverted U-shaped mounting system requires no tools, installs in seconds, and preserves complete bed rail functionality including raising, lowering, and rotating movements. The low-profile design allows the device to remain attached even when bed rails are lowered, fitting in the space between rail and mattress. The universal left/right configuration allows patients to position preferred items closest to their reach. The hospital-grade construction withstands repeated disinfection while meeting infection control requirements.

Still other aspects, features and advantages of the inven-tion are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The novel features of the invention are set forth with particularity in the appended claims. A better understanding of the features and advantages of the present invention will be obtained by reference to the following detailed descrip-tion that sets forth illustrative embodiments, in which the principles of the invention are utilized. The present inven-tion is illustrated by way of example, and not by way of limitation, in the figures of the accompanying drawings, in which like reference numerals refer to similar elements, and in which:

FIG. 2(*b*) is a front elevation view of the bedside attach-ment device of FIG. 1 shown with the bottle holder in deployed position and a phone and nurse-call positioned in their respective compartments.

DETAILED DESCRIPTION OF THE INVENTION

Figure 1:
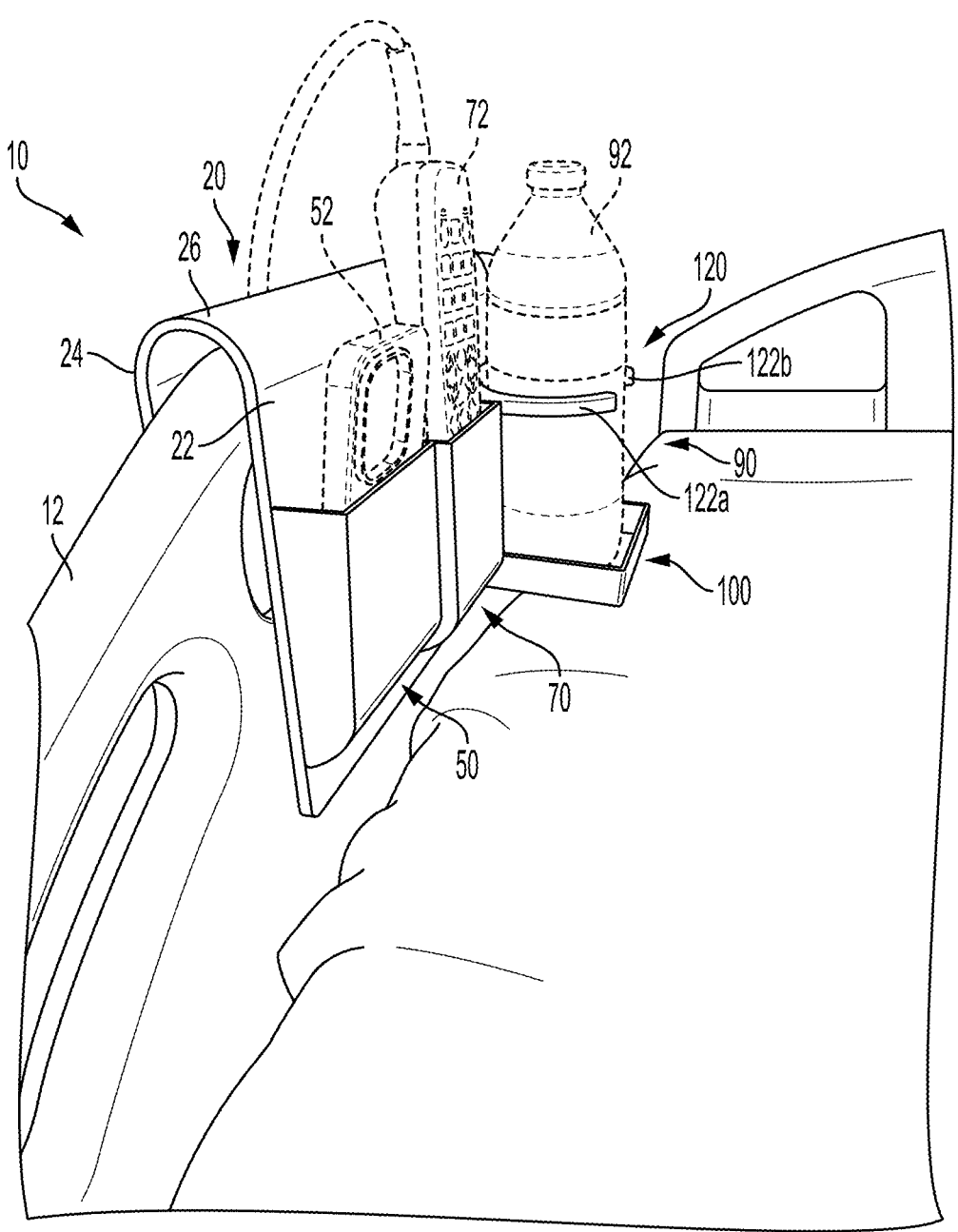
FIG. 1 is a perspective view of a bedside attachment device according to one embodiment of the present inven-tion, shown mounted on a hospital bed rail with the bottle holder in a deployed position.

The invention may be understood by referring to the following description and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Further-more, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not pre-clude the presence or addition of one or more other features, regions, integers, steps, operations, elements, components, and/or groups thereof.

Although some features may be described with respect to individual exemplary embodiments, aspects need not be limited thereto such that features from one or more exem-plary embodiments may be combinable with other features from one or more exemplary embodiments.

In accordance with certain aspects of an exemplary embodiment and with reference to FIGS. 1-5, a bedside attachment device 10 according to the present invention is shown. The device 10 is specifically configured for attachment to a hospital bed rail 12 and comprises a mounting system 20 with three dedicated compartments 50, 70, 90 mounted directly thereto for patient essential items.

The device 10 is designed to address the specific organizational needs of hospital patients who are confined to bed and require ready access to communication devices (mobile phones and nurse-call handsets) and beverages. Unlike generic bedside organizers, the present invention provides a carefully configured combination of three specific compartments, each optimized for a particular item commonly needed by hospital patients, with a low-profile design that maintains functionality even when bed rails are lowered.

Figure 3:
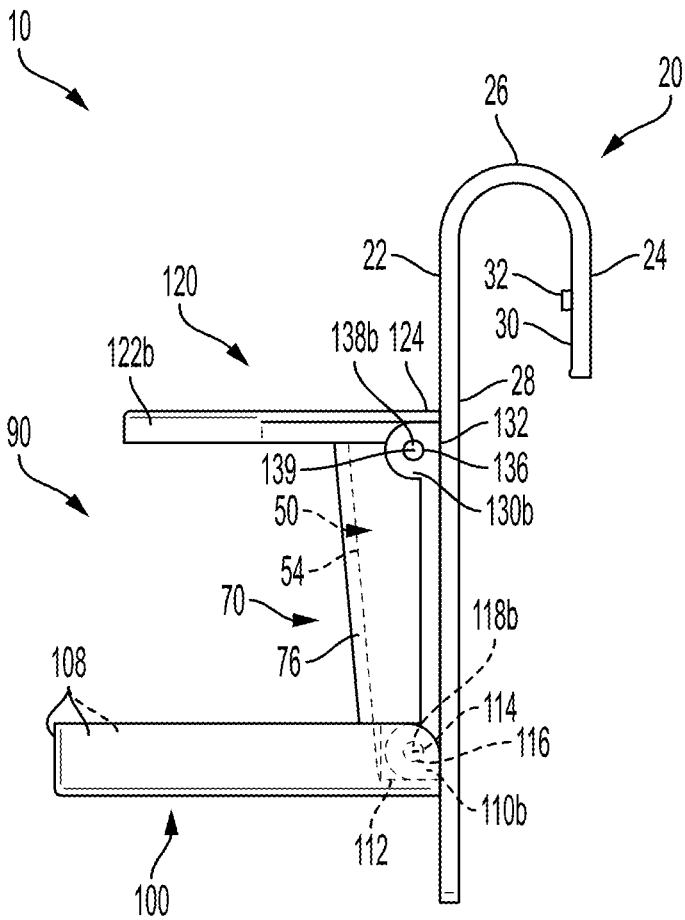
FIG. 3 is a side elevation view of the bedside attachment device of FIG. 1, showing the inverted U-shaped mounting bracket and the bottle holder in deployed position.
Figure 4:
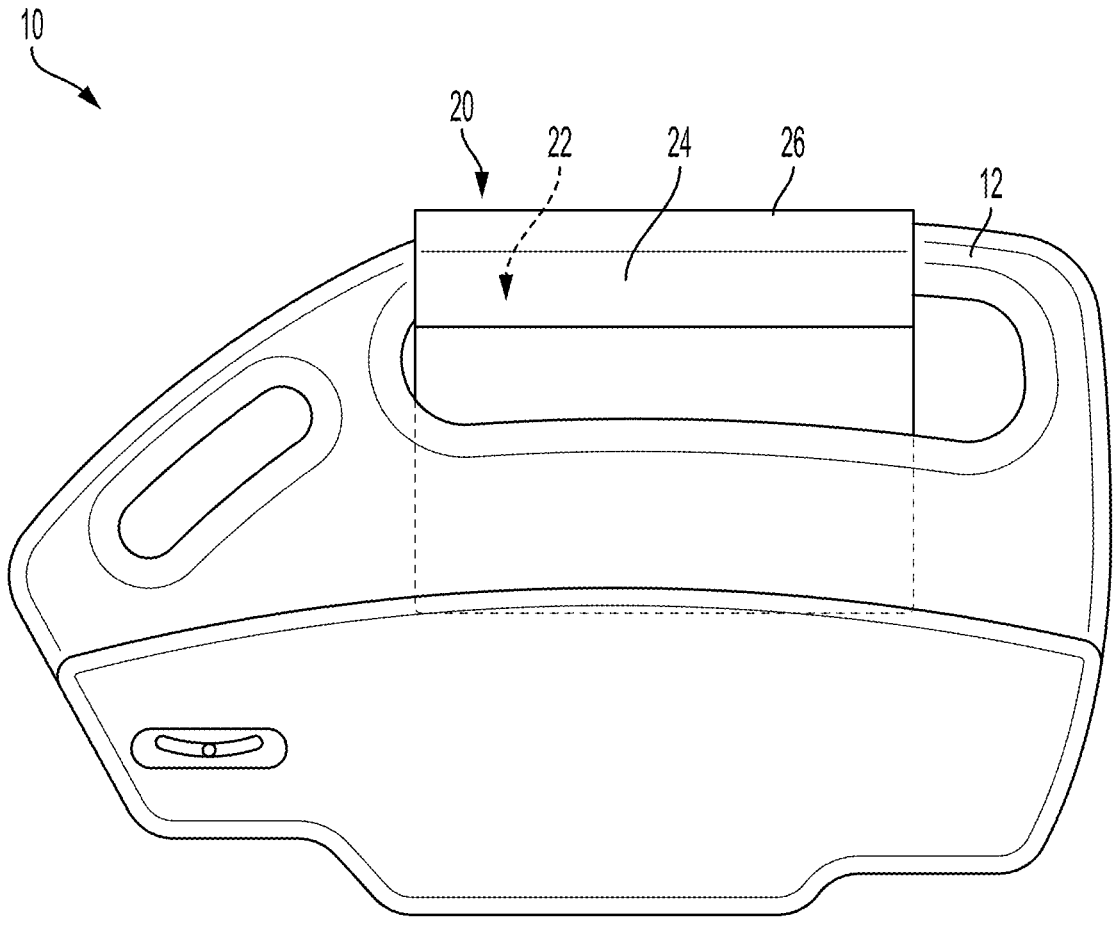
FIG. 4 is a rear elevation view of the bedside attachment device of FIG. 1 as seen from outside the bed, showing the second outer face of the mounting bracket.
Figure 9:
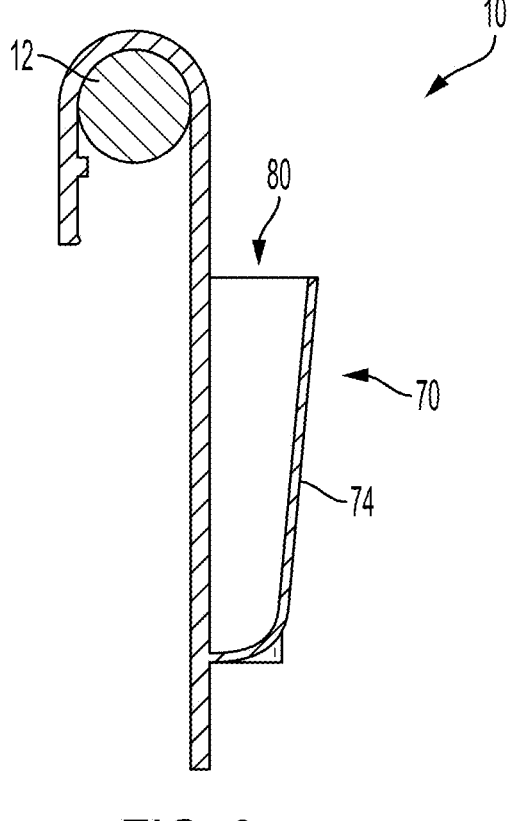
FIG. 9 is a side, cross-sectional view of the inverted U-shaped mounting bracket engaging a bed rail.

Referring particularly to FIGS. 3, 4, and 9, the mounting system 20 comprises an inverted U-shaped bracket structure that enables tool-less attachment to and removal from a hospital bed rail 12. The mounting system 20 includes a first inner face 22, a second outer face 24, and a connecting portion 26 that joins the first and second faces at their upper edges.

The first inner face 22 comprises an elongated planar surface having a height dimension sufficient to support all three compartments (phone cradle, nurse-call slot, and bottle holder) arranged adjacent to one another in a side-by-side configuration along the first inner face 22. The first inner face 22 faces toward the patient when the device 10 is mounted on a bed rail 12, positioning the compartments for convenient patient access. In the illustrated embodiment, the first inner face 22 may have a height in the range of approximately 5 to 10 inches, and preferably approximately 6 to 8 inches, providing adequate vertical space for the three compartments while remaining manageable in size for hospital room environments, although those skilled in the art may readily adapt the specific dimension of the first inner face 22, and of the other elements described herein, to accommodate varying bed and bed rail configurations.

The second outer face 24 comprises an elongated planar surface positioned opposite and parallel to the first inner face 22. The second outer face 24 faces away from the patient when mounted, toward the exterior side of the bed. The second outer face 24 may have a height dimension substantially less than the first inner face 22. The height of the second outer face 24 need only be sufficient to engage the outer side of the bed rail 12 and maintain stable attachment, typically in the range of approximately 1 to 4 inches, and preferably approximately 1 to 2 inches. This asymmetric configuration minimizes material usage and weight while providing stable mounting.

The connecting portion 26 extends between and joins the upper edges of the first inner face 22 and second outer face 24, forming the top of the inverted U-shape. The connecting portion 26 may be integrally molded with the first and second faces 22, 24 as a unitary structure, or may be a separate component joined by welding, adhesive bonding, mechanical fasteners, or other suitable attachment methods known in the art.

The spacing between the interior surface 28 of the first inner face 22 and the interior surface 30 of the second outer face 24 defines a rail-receiving channel 32. As shown in FIG. 9, the rail-receiving channel 32 is dimensioned to receive a standard hospital bed rail 12 with a close sliding fit. In the illustrated embodiment, the width of the rail-receiving channel 32 is in the range of approximately 1 to 3 inches, and preferably approximately 1 to 2 inches, sized to accommodate the top rail of common hospital bed models.

The mounting system 20 operates on a simple hook-over principle. To install the device 10, a user positions the inverted U-shaped bracket over the top rail of the hospital bed with the rail-receiving channel 32 aligned with the rail, then lowers the device until the interior surfaces 28, 30 engage both sides of the rail 12. The weight of the device 10 and friction between the interior surfaces 28, 30 and the rail 12 maintain the device in position during normal use. No clips, clamps, latches, screws, or other fastening mechanisms are required, enabling true tool-less installation and removal accomplished in seconds.

Importantly, the mounting system 20 preserves the full range of motion of the bed rail 12. Hospital bed rails typically articulate through various positions: raised for patient safety, lowered for patient entry/exit, and rotated inward or outward. The inverted U-shaped bracket may slide along the rail as it moves and does not interfere with any rail position or motion. This preservation of bed functionality is critical in hospital environments where bed adjustments are frequent and sometimes urgent.

When the bed rail 12 is lowered to its down position (typically resting against or near the mattress surface), the three dedicated compartments 50, 70, 90 are sized and configured with sufficiently low profile (particularly when the bottle holder is in its stowed position) to fit within the space between the lowered bed rail and the bed mattress without causing interference, binding, or requiring removal of the device. This enables the device 10 to remain attached and functional throughout all bed rail positions, enhancing convenience and ensuring patient items remain organized and accessible regardless of bed configuration.

The mounting system 20 also provides universal left/right mounting capability. The device 10 may be mounted on the left bed rail or right bed rail with equal functionality, allowing patients to position their preferred items (phone or bottle) closest to their dominant hand or preferred reach direction.

In an alternative configuration, mounting system 20 may include, for example, an adjustable-width rail-receiving channel in which the connecting portion 26 has an adjustable width, such as by way of a sliding track mechanism or telescoping structure, to allow the spacing between the first inner face 22 and second outer face 24 to be adjusted. In such an alternative configuration, a locking mechanism, such as a thumb screw, lever clamp, or friction lock, may secure the connecting portion 26 at the desired spacing.

Such an adjustable embodiment may accommodate a wider range of bed rail widths, making the device compatible with different hospital bed models and manufacturers, and may include by way of non-limiting example linear bearing slides, dovetail tracks, telescoping tubes, or other mechanisms known in the art for providing adjustable spacing.

In another alternative embodiment, the device may be provided in one of multiple pre-formed configurations particularly sized for specific populations, such as pediatric sizing and geriatric sizing to ease access to the compartments and their contents for those populations, and may further be provided with various printed graphic designs or other aesthetics (such as calming and/or child-friendly images) while maintaining infection control standards. Similarly, the device may be provided in single- or double-wide arrays to accommodate preferences of an individual patient, and may be in certain embodiments formed of high-temperature sterilizable-grade materials for specialty units that require environmental sterilization.

In yet another alternative embodiment, the interior surfaces 28, 30 may include resilient padding, friction-enhancing surfaces, or grip features such as ribs, texturing, or elastomeric inserts to increase friction and stability when mounted on the bed rail 12.

In still yet another alternative embodiment (not illustrated), the mounting system may include a safety tether or secondary retention feature such as a strap or hook that provides backup retention in case the device is accidentally knocked or jarred, while still maintaining the tool-less installation principle.

Next and turning to the details of the compartments on inner face 22, and with continuing reference to FIGS. 1-5, the device 10 includes three dedicated compartments mounted directly to the first inner face 22 of the mounting system 20: namely, phone cradle compartment 50, nurse-call handset slot compartment 70, and bottle holder compartment 90.

Each compartment 50, 70, 90 is a standalone structure independently mounted to the first inner face 22. Unlike some prior art devices that feature a separate housing or caddy structure which itself contains multiple pockets, the present invention mounts each compartment directly to the mounting system, eliminating unnecessary intermediate structures. This direct-mount configuration provides several advantages: simplified construction with fewer parts, reduced weight, enhanced cleanability by eliminating crevices between a housing and compartments, and a minimized profile that enables the device to fit between the lowered bed rail and mattress.

The term "dedicated compartment" as used herein means a storage space specifically sized, shaped, and configured for a particular item type, as distinguished from generic pockets or universal storage spaces. Each dedicated compartment is optimized for its intended item in terms of dimensions, access opening, retention features, and positioning.

The three compartments 50, 70, 90 are arranged in a fixed spatial relationship, meaning their positions relative to one another do not change during normal use. In the illustrated embodiment, the three compartments are arranged in a generally side-by-side configuration along the first inner face 22, though other arrangements (e.g., vertically stacked, diagonal, or hybrid configurations) are within the scope of the invention as long as the specific three-compartment combination is present.

This specific three-compartment combination of phone cradle, nurse-call handset slot, and bottle holder represents a novel configuration specifically addressing the needs of hospital patients. The inventor recognized through observation and experience that these three items (mobile phone, nurse-call device, and beverage) are the most frequently accessed and problematic items for bedridden patients. By integrating dedicated spaces for all three items into a single organized unit that mounts directly to the bed rail and maintains compatibility with bed rail articulation, the invention solves the chronic disorganization problem in hospital rooms.

Figure 2A:
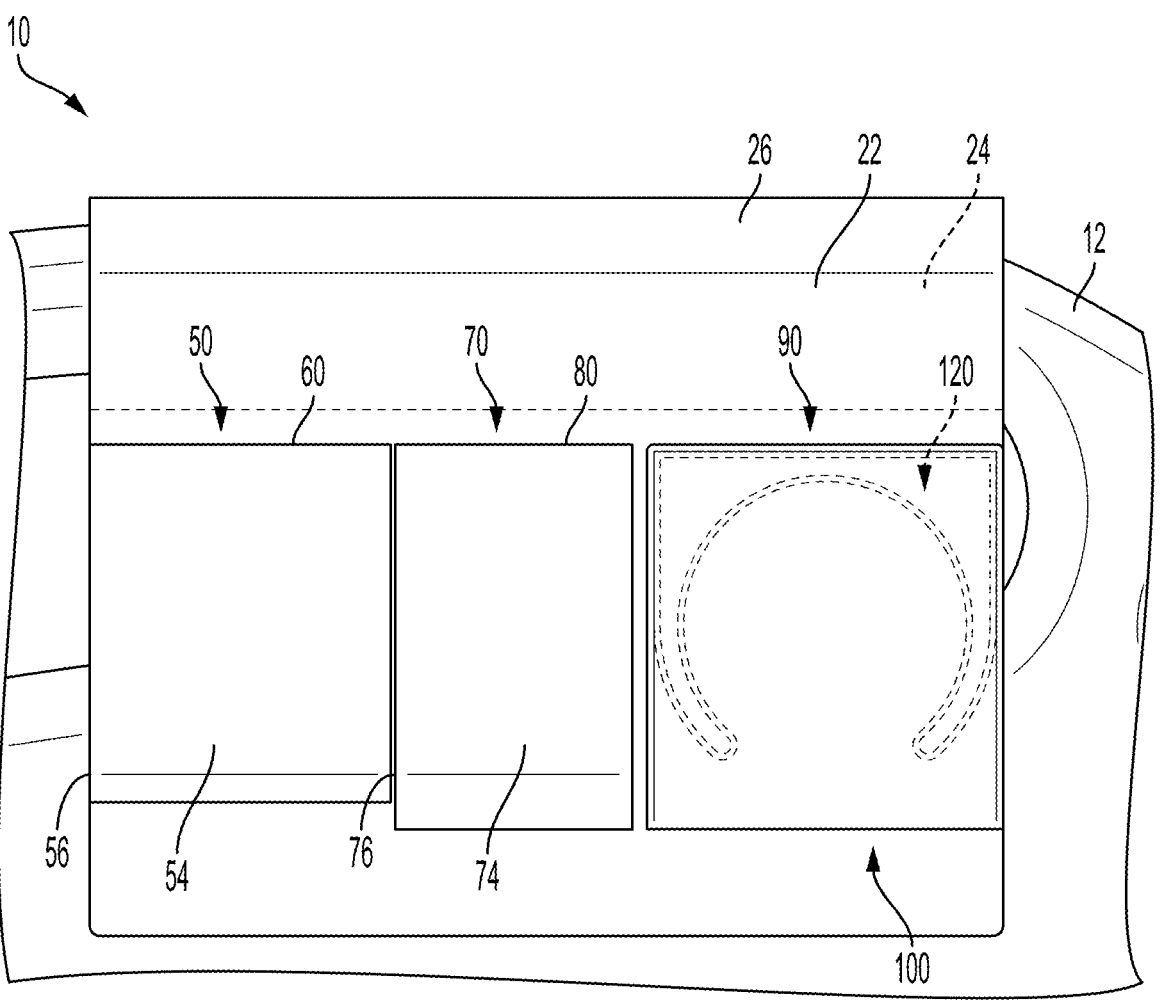
FIG. 2(*a*) is a front elevation view of the bedside attach-ment device of FIG. 1 as seen from the patient's perspective, showing the first inner face and the spatial arrangement of the three compartments.
Figure 2B:
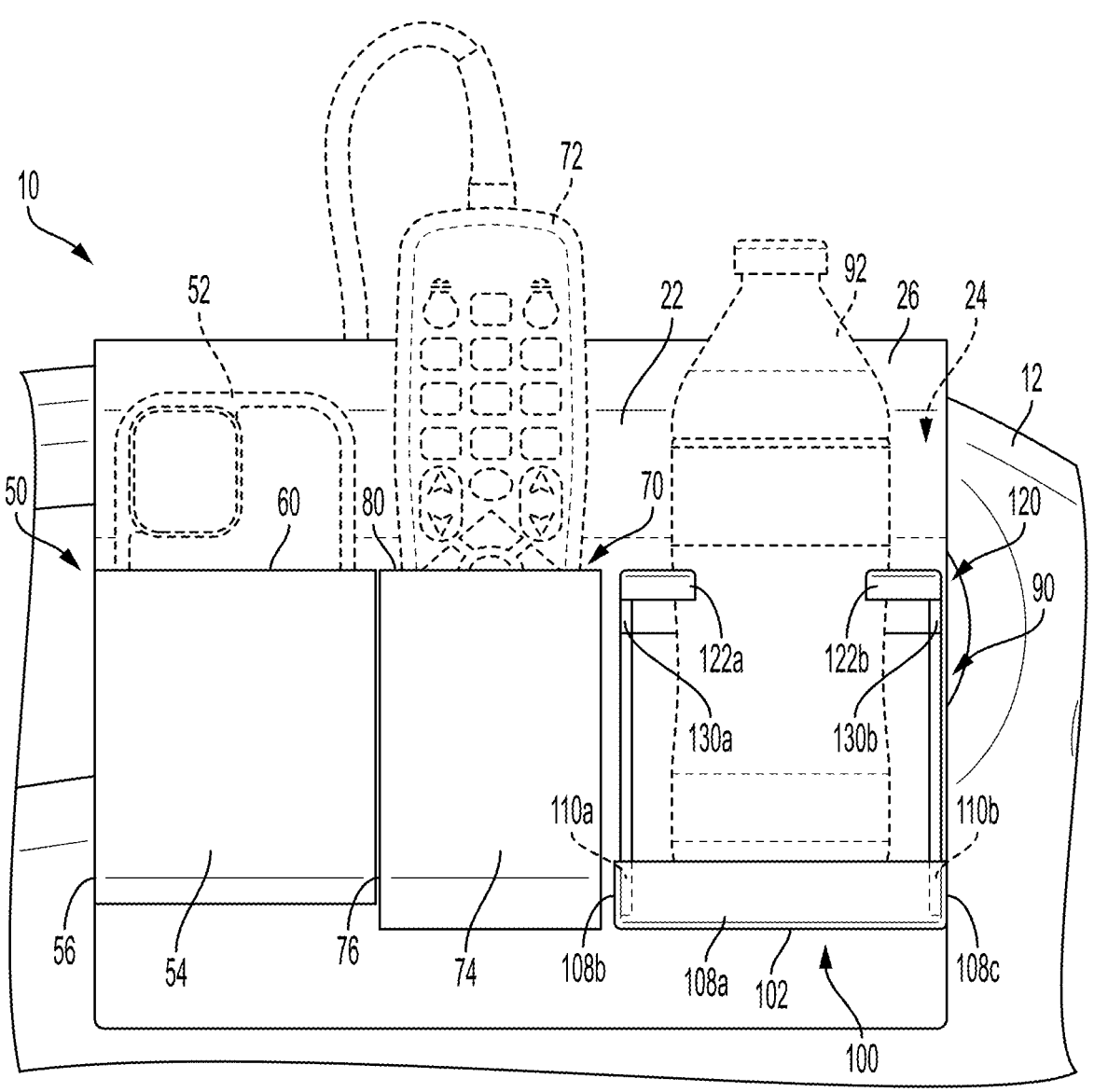
Figure 5:
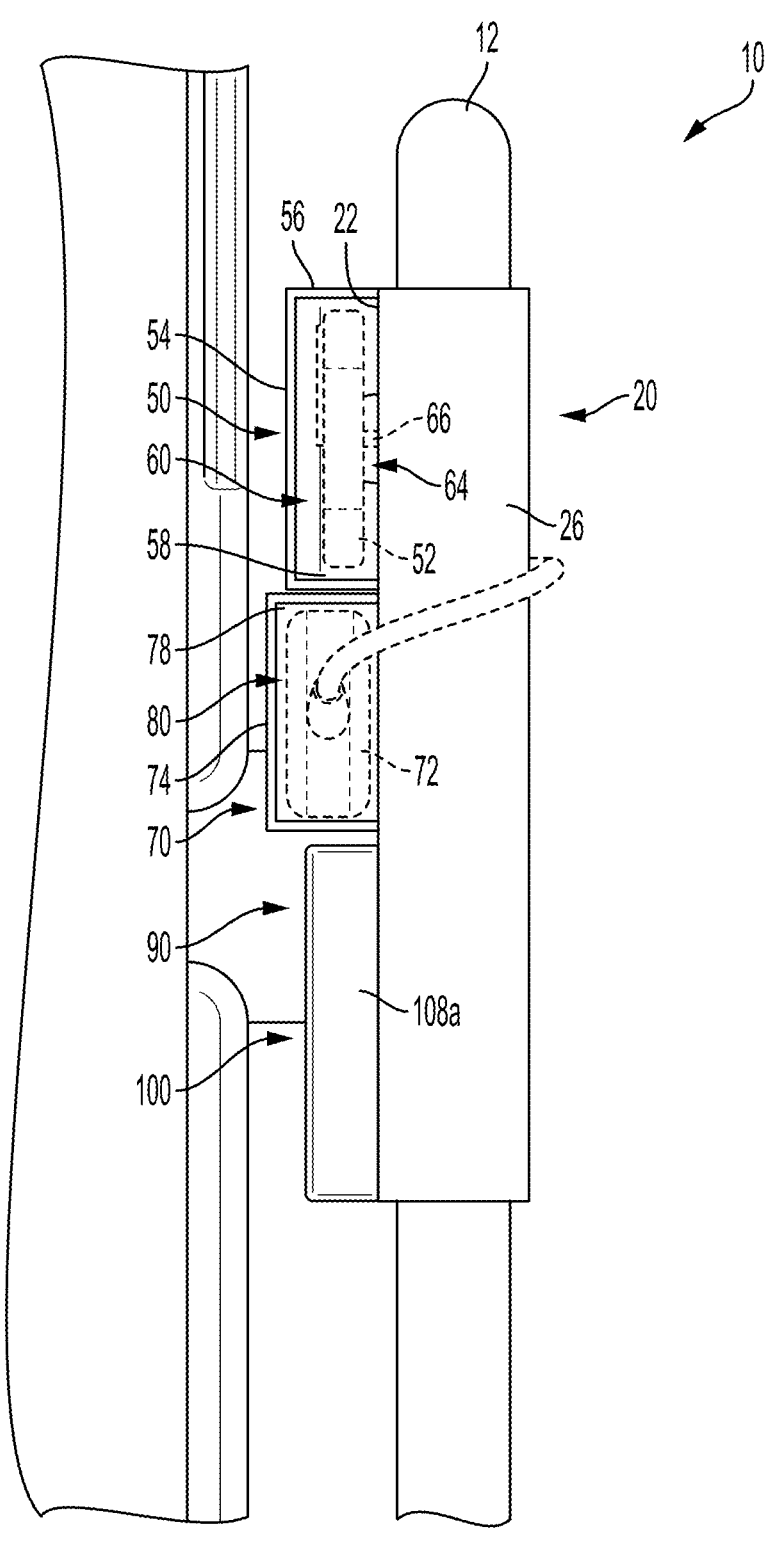
FIG. 5 is a top view of the bedside attachment device of FIG. 1 with the bottle holder in a stowed position, showing the low-profile configuration.
Figure 6:
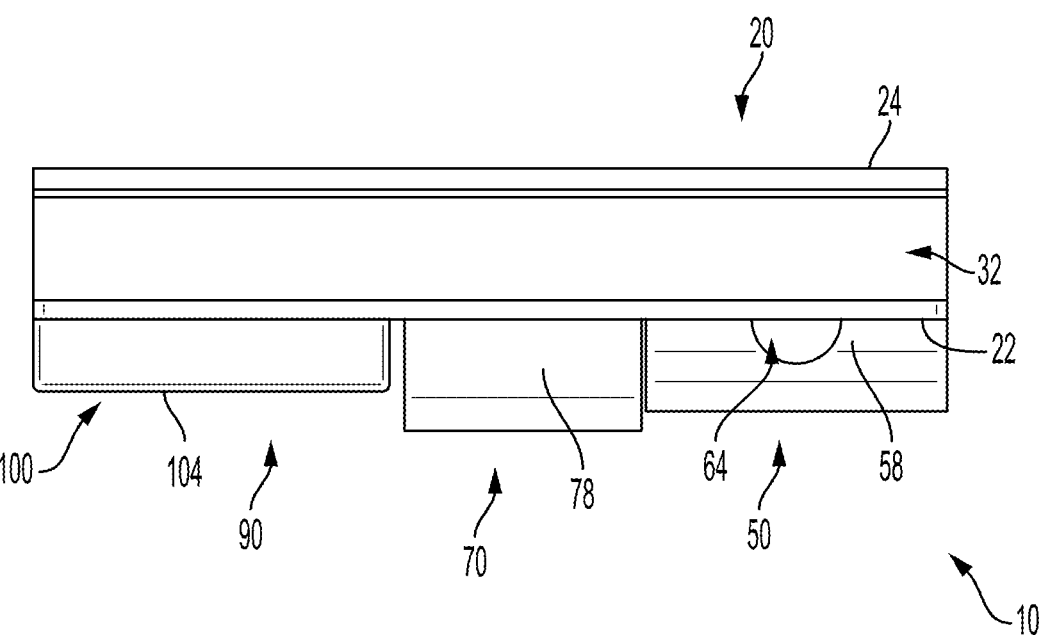
FIG. 6 is a bottom view of the bedside attachment device and showing the phone cradle compartment with the pass-through opening for charging cables.

Referring to FIGS. 1, 2, and 6, the phone cradle compartment 50 comprises a pocket-like structure configured to receive and support a mobile phone 52 (shown in phantom in FIGS. 1m 2(b) and 5). The phone cradle compartment 50 includes an outer wall 54, two side walls 56, a bottom wall 58, and an open top 60. The open top 60 allows the phone 52 to be inserted and removed by vertical motion.

In an exemplary embodiment, the phone cradle compartment 50 is mounted directly to the first inner face 22 by integral molding, welding, mechanical fasteners, adhesive bonding, or other suitable attachment methods. In this exemplary embodiment, the compartment 50 and the first inner face 22 are integrally molded as a unitary structure, eliminating seams and crevices that could harbor contaminants.

The dimensions of the phone cradle compartment 50 are selected to accommodate common smartphone sizes. In the illustrated exemplary embodiment, the interior width (between side walls 56) is approximately 3 to 4 inches, the interior depth (from outer wall 54 to the first inner face 22) is approximately 0.5 to 1.5 inches, and the height (from bottom wall 58 to open top 60) is approximately 3 to 4 inches. These dimensions accommodate smartphones in the range of standard sizes including iPhone, Samsung Galaxy, Google Pixel, and similar devices, with or without protective cases while ensuring ready and easy access.

Phone cradle compartment 50 includes a pass-through opening 64 formed in the bottom wall 58. The pass-through opening 64 allows a charging cable 66 (shown in phantom in FIG. 5) to be routed into the compartment 50 from below, with the cable connector inserted into the phone's charging port while the phone rests in the compartment. This enables the phone to charge while stored, eliminating the need to remove the phone for charging.

The pass-through opening 64 may be a simple slot, a circular or oval hole, or a more complex shape such as a keyhole or funnel shape that guides the cable. In the illustrated embodiment, the pass-through opening 64 comprises an elongated slot approximately 0.5 to 1 inches by 0.25 to 0.5 inches, sufficient to pass USB cables, Lightning cables, USB-C cables, and similar charging cable connectors.

The positioning of the pass-through opening 64 at the bottom of the phone cradle compartment 50 is advantageous because it allows the cable to enter from below, minimizing visual clutter and preventing the cable from interfering with phone insertion or removal. The cable 66 may hang down below the device 10 or be routed along the bed rail to a power outlet.

The phone cradle compartment 50 may optionally include retention features to prevent the phone from falling out if the bed is moved or jarred. Such retention features may include resilient fingers or tabs that extend partially across the open top 60, friction pads on interior surfaces, or adjustable retention straps. However, in many embodiments, simple gravity retention is sufficient given the stable mounting of the device and the typical orientation with the open top 60 facing upward.

The depth dimension of the phone cradle compartment 50 is kept to a minimum consistent with functional phone retention, contributing to the overall low profile of the device that enables fitting between the lowered bed rail and mattress.

Figure 7:
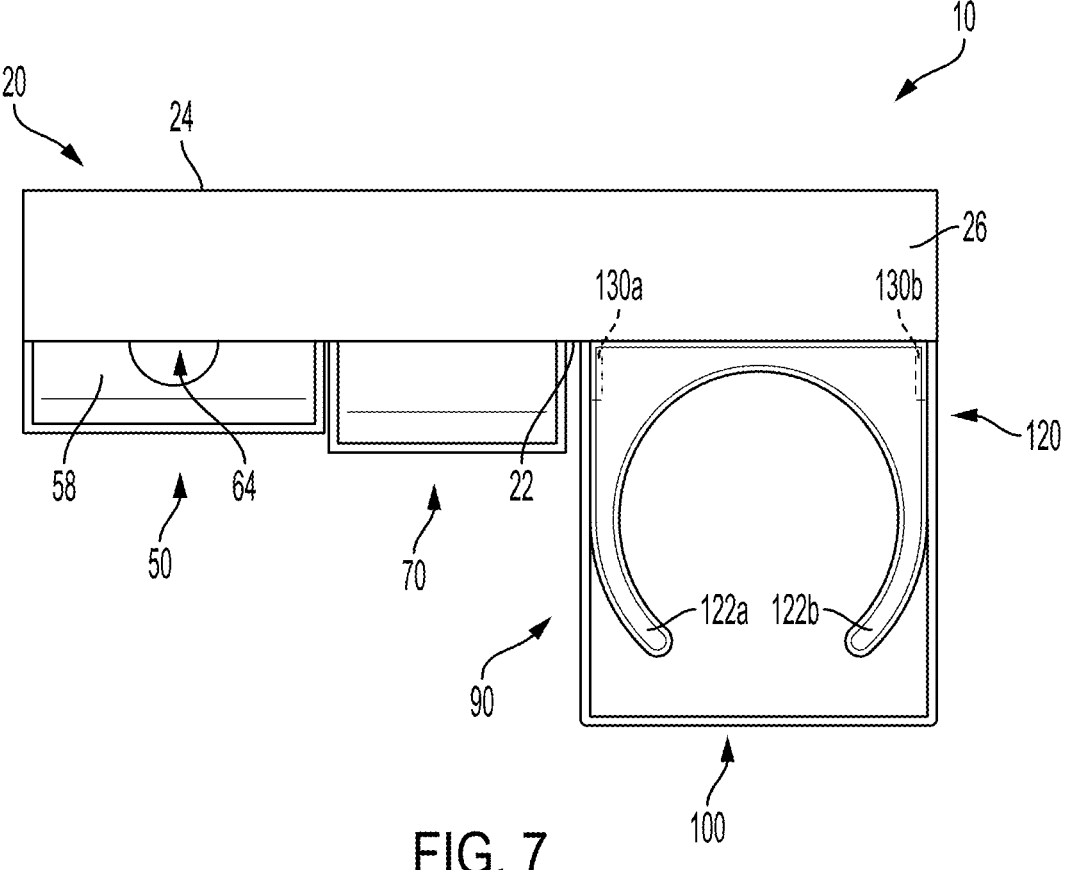
FIG. 7 is a top view of the bedside attachment device of FIG. 1 with the bottle holder in a deployed position.
Figure 8:
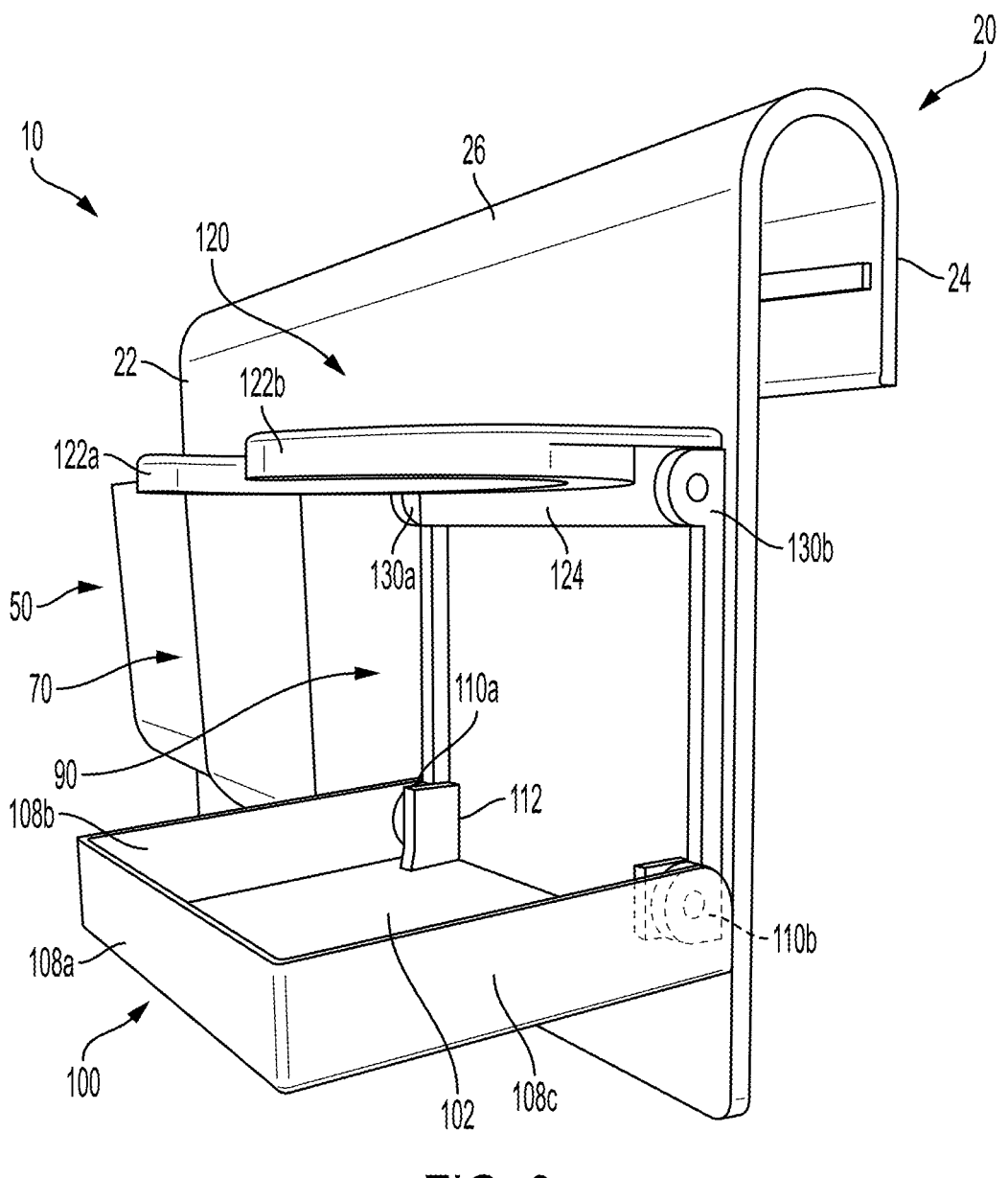
FIG. 8 is a detailed perspective view of the foldable bottle holder mechanism showing the hinge brackets and pivot pins.

Next and with reference to FIGS. 1, 2, and 7, the nurse-call handset slot compartment 70 comprises a pocket-like structure configured to receive and support a nurse-call handset 72 (shown in phantom in FIGS. 1, 2(b) and 5). Hospital nurse-call systems typically include a handset or button panel connected to the bed by a cable, which the patient uses to summon nursing staff. These handsets are critical safety devices but are notorious for falling behind beds or becoming tangled in bedding.

The nurse-call handset slot compartment 70 includes an outer wall 74, two side walls 76, a bottom wall 78, and an open top 80. The open top 80 allows the handset 72 to be inserted and removed by vertical motion.

Like the phone cradle compartment 50, the nurse-call handset slot compartment 70 is mounted directly to the first inner face 22 as a standalone structure, preferably by integral molding to form a unitary construction with the mounting system 20. This direct mounting eliminates unnecessary intermediate housing structures and contributes to the low-profile design.

The dimensions of the nurse-call handset slot compartment 70 are selected to accommodate common nurse-call handset designs. In the illustrated embodiment, the interior width (between side walls 76) is approximately 2 to 4 inches, the interior depth (from outer wall 74 to the first inner face 22) is approximately 0.75 to 2 inches, and the height (from bottom wall 78 to open top 80) is approximately 3 to 5 inches. These dimensions accommodate typical nurse-call handsets including button panels, remote controls, and combination devices.

The provision of a dedicated nurse-call handset slot compartment 70 represents a significant innovation. Prior art bedside organizers do not specifically address nurse-call handset storage, instead providing only generic pockets. The present invention recognizes the unique importance of the nurse-call device in the hospital setting and provides dedicated storage that keeps this critical safety device accessible at all times.

The nurse-call handset slot compartment 70 is positioned separately from the phone cradle compartment 50, preventing the two devices from becoming confused or interfering with one another. In the illustrated embodiment, the nurse-call compartment 70 is positioned adjacent to the phone cradle compartment 50, though other relative positions are possible.

As with the phone cradle compartment, the depth dimension of the nurse-call handset slot compartment 70 is minimized to contribute to the overall low profile necessary for compatibility with lowered bed rails.

Next and with reference to FIGS. 1, 2(*a*), 2(*b*), 7 and 8, the bottle holder compartment 90 comprises a foldable bottle holder mechanism that transitions between a deployed position (FIGS. 1, 2(*b*), 7 and 8) for holding a beverage container 92 and a stowed position (FIGS. 2(*a*) and 5) in which the holder is folded against the first inner face 22 to minimize space consumption.

The bottle holder compartment 90 includes two pivotable components: a base assembly 100 and an upper holding bracket assembly 120. Both components pivot independently via hinge mechanisms mounted directly to the first inner face 22, consistent with the direct-mount design principle of the invention.

The foldable nature of the bottle holder compartment 90 is particularly important for enabling the device to fit between the lowered bed rail and mattress. When stowed in the vertical position, the bottle holder adds minimal depth to the overall device profile, allowing the entire device to remain attached to the bed rail even when the rail is in its lowest position.

The base assembly 100 comprises a base panel 102 having a generally rectangular or square planar shape. The base panel 102 includes a bottom surface 104 upon which a beverage container rests, and a perimeter edge 106. Three sidewalls 108 extend upward from the perimeter edge 106: a front sidewall 108*a* positioned at the outer edge of the base panel (farthest from the first inner face 22 when deployed), and two side sidewalls 108*b*, 108*c* positioned along the left and right edges of the base panel. The rear edge of the base panel 102 (closest to the first inner face 22 when deployed) has no sidewall, allowing this edge to pivot close to the first inner face 22.

The sidewalls 108 are relatively short, typically 0.5 to 1.5 inches in height. The sidewalls 108 serve to retain the beverage container on the base panel 102 and prevent sliding, but are not tall enough to interfere with placement or removal of the container or to add excessive depth when stowed.

The base panel 102 is pivotably mounted to the first inner face 22 via a first pair of hinge brackets 110*a*, 110*b*. The first hinge brackets 110*a*, 110*b* are mounted directly to the first inner face 22 in spaced-apart positions corresponding to the left and right sides of the base assembly 100. Each first hinge bracket 110*a*, 110*b* includes a mounting portion 112 that attaches to the first inner face 22 (by mechanical fasteners, welding, adhesive, integral molding, or other suitable attachment methods), and a pivot portion 114 that includes a pivot opening 116.

The base panel 102 includes pivot pins 118*a*, 118*b* extending inwardly from the left and right side walls 108*b*, 108*c*. The pivot pins 118*a*, 118*b* are received within the pivot openings 116 of the first hinge brackets 110*a*, 110*b*, allowing the base assembly 100 to rotate about a horizontal pivot axis 119.

In the stowed position (FIG. 5), the base assembly 100 is rotated upward so that the base panel 102 is oriented vertically and positioned flush against or closely adjacent to the first inner face 22. In this position, the bottle holder occupies minimal space and presents a low profile that contributes to the device's ability to fit between the lowered bed rail and mattress.

In the deployed position (e.g., FIG. 3), the base assembly 100 is rotated downward approximately 90 degrees so that the base panel 102 is oriented horizontally and extends outward from the first inner face 22. In this position, the base panel 102 provides a stable platform for supporting a beverage container. The range of rotation is limited by contact between the lower edges of the side walls 108*b*, 108*c* and the first inner face 22, which provides a positive stop preventing over-rotation beyond the horizontal position.

The upper holding bracket assembly 120 of bottle holder compartment 90 comprises a bracket structure having two arc arms 122*a*, 122*b* that extend in curved paths designed to partially wrap around the upper portion of a beverage container 92. The arc arms 122*a*, 122*b* are connected at their inner ends to a pivot mounting structure 124.

The upper holding bracket assembly 120 is pivotably mounted directly to the first inner face 22 via a second pair of hinge brackets 130*a*, 130*b*. The second hinge brackets 130*a*, 130*b* are positioned above the first hinge brackets 110*a*, 110*b* and are vertically aligned therewith so that the upper holding bracket assembly 120 and base assembly 100 pivot about parallel horizontal axes.

Each second hinge bracket 130*a*, 130*b* includes a mounting portion 132 that attaches directly to the first inner face 22, and a pivot portion 134 that includes a pivot opening 136. The pivot mounting structure 124 of the upper holding bracket includes pivot pins 138*a*, 138*b* that are received within the pivot openings 136, allowing the upper holding bracket assembly 120 to rotate about a horizontal pivot axis 139.

In the stowed position (FIG. 5), the upper holding bracket assembly 120 is rotated downward so that the arc arms 122*a*, 122*b* are oriented vertically and positioned flush against or closely adjacent to the first inner face 22. In this position, the arc arms 122*a*, 122*b* are positioned within or behind the vertically-oriented base assembly 100, resulting in a compact stowed configuration that maintains the low profile necessary for fitting between the lowered bed rail and mattress.

In the deployed position (FIGS. 1, 2(*b*), 3, 7 and 8), the upper holding bracket assembly 120 is rotated upward approximately 90 degrees so that the arc arms 122*a*, 122*b* extend horizontally outward from the first inner face 22. The arc arms 122*a*, 122*b* are positioned above the base panel 102 and curve inward to partially encircle a beverage container 92 resting on the base panel. This configuration securely retains the beverage container, preventing it from tipping or being accidentally knocked off the base panel.

The arc arms 122*a*, 122*b* may have various curvature profiles. In one embodiment, the arc arms extend in semi-circular arcs that wrap approximately 180 degrees around the container. In another embodiment, the arc arms extend in partial arcs of approximately 90 to 135 degrees. The spacing between the arc arms 122*a*, 122*b* is selected to accommodate common beverage container diameters, typically approximately 2.5 to 4.0 inches, suitable for standard water bottles, soda cans, coffee cups, and similar containers.

To deploy the bottle holder from the stowed position to the deployed position, the user grasps the base assembly 100 and/or upper holding bracket assembly 120 and rotates the base assembly 100 downward and the upper holding bracket assembly 120 upward, each to their horizontal positions. To stow the bottle holder, the user rotates both components in the opposite directions to their vertical positions.

In the deployed position, the upper holding bracket assembly 120 may be held in place by various retention mechanisms. In one embodiment, friction between the pivot pins 138*a*, 138*b* and the pivot openings 136 may provide sufficient resistance to prevent unintended rotation. The friction may be achieved through tight tolerances, resilient materials, or textured surfaces on the pivot pins or openings.

In another embodiment, a detent mechanism may provide positive positioning. The detent may comprise a spring-loaded ball or pin on one pivot component that engages a recess or notch on the mating pivot component when the deployed position is reached, providing tactile feedback and retention.

In yet another embodiment, a snap-fit mechanism may secure the deployed position. For example, the arc arms 122*a*, 122*b* or pivot mounting structure 124 may include flexible tabs that snap into engagement with corresponding features on the first inner face 22 or hinge brackets 130*a*, 130*b* when the deployed position is reached.

In still another embodiment, a magnetic retention system may use magnets embedded in the pivot mounting structure 124 and the first inner face 22 or hinge brackets 130*a*, 130*b* to provide attractive force that holds the deployed position.

The retention mechanism should provide sufficient holding force to maintain the deployed position during normal use (including when a full beverage container is placed on the base), while still allowing easy manual deployment and stowing by the patient without requiring excessive force.

In an alternative embodiment (not illustrated), the base assembly and upper holding bracket assembly may be coupled by a linkage mechanism such that deployment of the base assembly may automatically deploy the upper holding bracket, and stowing the base assembly may automatically stow the upper holding bracket. This simplifies operation to a single motion.

In another alternative embodiment (not illustrated), the bottle holder may comprise a single unitary piece that pivots between stowed and deployed positions, rather than separate base and upper bracket components.

In yet another alternative embodiment (not illustrated), the bottle holder may comprise a sliding or telescoping mechanism rather than a pivoting mechanism, extending outward from the first inner face via linear motion rather than rotational motion.

As described above, the phone cradle compartment 50 includes a pass-through opening 64 that serves as a basic cable management feature, allowing charging cables to be routed in an organized manner. In alternative configurations, additional cable management features may be provided including, by way of non-limiting example: grooves, tracks, or recesses molded into the exterior or interior surfaces of the first inner face 22 or the compartments that guide cables along defined paths, preventing tangling and maintaining a neat appearance; spring clips, snap-fit holders, or loop fasteners mounted to the first inner face 22 or compartments that secure cables at intervals, preventing drooping or swinging; additional pass-through openings positioned at various locations on the first inner face 22 or compartments that allow cables to be routed between compartments or from one side of the device to the other; posts, hooks, or apertures configured to receive cable ties, allowing users to bundle and secure multiple cables; and adhesive-backed cable organizers that may comprise removable and repositionable adhesive strips or pads that can be attached to the first inner face 22 or compartment surfaces to hold cables in user-selected positions. The cable management features may be integrated into the initial design of the device or may be provided as modular accessories that can be added by the user based on their specific needs and the number of cables requiring management (phone charger, nurse-call cable, tablet charger, etc.).

The device 10 is preferably constructed from materials suitable for the hospital environment, meeting requirements for durability, infection control, and safety. In the preferred embodiment, the mounting system 20 (including the first inner face 22, second outer face 24, and connecting portion 26) and the three dedicated compartments 50, 70, 90 are constructed from medical-grade thermoplastic materials, specifically acrylonitrile butadiene styrene (ABS) or polycarbonate (PC), or a blend thereof (ABS/PC). These materials provide excellent strength, rigidity, impact resistance, and dimensional stability.

Preferably, the materials include antibacterial additives. Antibacterial agents such as silver ions, copper compounds, or organic antimicrobials may be compounded into the plastic during manufacturing, providing ongoing antimicrobial properties that inhibit bacterial growth on the device surfaces. This addresses infection control concerns in hospital environments where surface contamination is a significant risk.

All surfaces of the device 10, and particularly the exterior surfaces exposed to touch or environmental contamination, are smooth and non-porous. Sharp corners and edges are avoided or radiused. Crevices, seams, and joints are minimized or sealed to prevent accumulation of contaminants. These design features ensure the device can be effectively cleaned and disinfected using standard hospital cleaning protocols including quaternary ammonium compounds, hydrogen peroxide solutions, bleach solutions, and alcohol wipes.

The device may be manufactured as a unitary molded structure (mounting system and all three compartments formed as one piece) or may be assembled from multiple components that are welded, snap-fit, or fastened together. Ultrasonic welding is particularly suitable for creating strong, sealed joints without mechanical fasteners. The preferred construction method is unitary molding or ultrasonic welding to eliminate crevices and create smooth, continuous surfaces optimized for infection control.

The hinge brackets 110*a*, 110*b*, 130*a*, 130*b* and pivot pins 118*a*, 118*b*, 138*a*, 138*b* may be manufactured from the same material as the mounting system and compartments, or from different materials selected for specific properties. For example, the pivot pins may be stainless steel or hardened plastic to provide wear resistance and smooth pivoting action over many deployment/stowage cycles.

In alternative embodiments, the device may be constructed from other materials including, by way of non-limiting example: aluminum or aluminum alloys to provide a lightweight, strong, corrosion-resistant option, suitable for anodizing in various colors and offering a premium appearance and excellent durability; stainless steel to provide an extremely durable, easily sterilized option, providing the highest level of hygiene, suitable for critical care environments with the highest infection control requirements; anti-microbial-coated metals, such as steel or aluminum with applied antimicrobial coatings that provide additional bacterial inhibition; and silicone or thermoplastic elastomers (TPE) that may be used for grip surfaces, padding on interior surfaces of mounting system, or flexible components.

The color of the device may be selected to match hospital environments. For example, neutral colors such as white, light gray, beige, or soft blue may be used to blend with typical hospital room décor. The materials may be pigmented during manufacturing or may be painted or powder-coated after molding.

While dimensions may vary based on specific design choices and intended applications, exemplary dimensions for one embodiment are as follows:

Overall device height: Approximately 8 to 12 inches, allowing comfortable reach from bed height while fitting within typical bedside space constraints.

Overall device depth in stowed configuration: Approximately 1 to 2 inches (measured from the outer surface of the second outer face 24 to the outer surface of the first inner face 22 with all compartments in low-profile/stowed position), enabling the device to fit between the lowered bed rail and mattress.

Rail-receiving channel width: Approximately 0.5 to 1.5 inches (spacing between interior surfaces 28, 30), sized for standard hospital bed rails.

First inner face height: Approximately 6 to 8 inches (taller face, supporting compartments).

Second outer face height: Approximately 1 to 2 inches (shorter face, providing outer rail engagement).

Phone cradle compartment: Approximately 3-4 inches wide, 3-4 inches tall, 0.5-1.5 inches deep.

Nurse-call handset slot: Approximately 2-4 inches wide, 3-5 inches tall, 0.75-2 inches deep.

Bottle holder base panel: Approximately 4-6 inches square or rectangular, with sidewalls approximately 0.75-1 inch tall.

Arc arms of upper holding bracket: Extending approximately 3-5 inches outward from first inner face when deployed, curved to accommodate containers of approximately 2.5-4 inches diameter.

These dimensions provide a balanced design that accommodates the intended items while remaining manageable in size for hospital environments and, critically, maintaining a low enough profile to fit between the bed rail and mattress when the rail is lowered. The dimensions may be scaled up or down to create variant embodiments for different applications (pediatric beds, bariatric beds, home use, etc.).

As noted above, the device 10 may be mounted on either the left or right bed rail with equal functionality. This universal mounting capability is inherent in the symmetric nature of the inverted U-shaped mounting system 20, which does not have a preferred orientation. Thus, when mounted on the left rail, the first inner face 22 (with its three compartments) faces toward the left side of the bed and is accessible to a patient lying in bed. When mounted on the right rail, the first inner face 22 faces toward the right side of the bed. In both configurations, the second outer face 24 faces away from the bed toward the exterior. The ability to choose left or right mounting allows patients to position the device on their preferred side based on dominant handedness, room layout (location of power outlets for phone charging), or simply personal preference. Family members visiting from a particular side of the bed may also prefer a certain orientation.

In an alternative embodiment of the present invention, one or more of the three compartments 50, 70, 90 may be configured as removably attachable modular units that can be selectively positioned at different locations on the first inner face 22. In this modular configuration, the first inner face 22 includes a plurality of discrete attachment locations distributed horizontally along its length. For example, multiple attachment locations may be spaced at regular vertical intervals (e.g., approximately 2-3 inches apart), though more or fewer locations may be provided depending on the overall height of the first inner face and desired positioning granularity.

Each attachment location may include a receiving interface configured to engage with a complementary mounting interface provided on the rear surface of each modular compartment unit. The compartment may be attached at any selected attachment location and subsequently removed and repositioned at a different attachment location to accommodate user preferences such as dominant handedness, reach limitations, or frequency of access to particular items.

The removable attachment between compartments and attachment locations may be achieved through various removable coupling mechanisms known in the art, including but not limited to: (i) dovetail or sliding track engagement wherein the first inner face includes one or more tracks and each compartment includes a complementary rail that slides into the track and can be locked at discrete positions; (ii) hook-and-slot mechanisms wherein compartments include hooks that engage corresponding slots at each attachment location, allowing the compartment to be hung and removed; (iii) snap-fit connections wherein resilient clips or flexible elements on either the compartment or the attachment location engage corresponding features to secure the compartment, with the connection releasable by applying pull force or actuating a release mechanism; or magnetic attachment wherein magnets or ferromagnetic elements are positioned at each attachment location and on each compartment, providing attractive force to secure the compartment while allowing removal by overcoming the magnetic attraction.

These coupling mechanisms are well-known in the field of modular furniture, storage systems, and medical device attachments, and one of ordinary skill in the art would readily understand how to implement them in the context of the present bedside attachment device.

The modular configuration allows patients or caregivers to customize compartment positioning based on individual needs. For example, a patient with limited reach may position all compartments within a narrow vertical range, while a patient who frequently accesses beverages may position the bottle holder at the topmost position for easiest access. Compartments can be repositioned quickly without tools, accommodating changing patient needs during hospitalization.

In some modular embodiments, all three compartments are removably attachable, while in other embodiments, only one or two compartments are modular with the remaining compartment(s) fixed in position.

A distinguishing feature of the present invention is the low-profile design that enables the device 10 to remain attached to the bed rail even when the rail is lowered to its down position. Hospital bed rails typically articulate between a raised position (for patient safety) and a lowered position (for patient access, transfers, or when the bed is unoccupied). In the lowered position, the rail typically rests on or near the mattress surface, creating a narrow gap between the rail and mattress. This design feature provides significant practical advantages. Patients and caregivers are not required to remove the device when adjusting bed rails, saving time and preventing items from being displaced or lost. The device remains accessible and functional in all bed configurations. Items stored in the compartments remain secure and organized regardless of bed position.

While the device is designed to fit when the bed rail is lowered, it can also be easily removed if desired by simply lifting it off the bed rail, consistent with the tool-less installation and removal principle.

The method of using the device 10 comprises the following steps:

Step 1—Positioning: The user positions the device 10 over the top rail of the hospital bed with the inverted U-shaped mounting system aligned so that the rail-receiving channel 32 is centered over the rail and the first inner face 22 (with compartments) faces toward the patient.

Step 2—Attachment: The user lowers the device until the interior surfaces 28, 30 of the mounting system 20 engage both sides of the bed rail 12. The device is now securely attached without tools, screws, or clamps.

Step 3—Phone Storage: The patient or caregiver places a mobile phone 52 into the phone cradle compartment 50, optionally routing a charging cable 66 through the pass-through opening 64 to enable charging.

Step 4—Nurse-Call Storage: The patient or caregiver places the nurse-call handset 72 into the nurse-call handset slot compartment 70, with the handset cable routed through the cable relief notch 82 if present.

Step 5—Bottle Holder Deployment: The patient or caregiver deploys the bottle holder by rotating the base assembly 100 and upper holding bracket assembly 120 from their stowed positions to their deployed positions.

Step 6—Beverage Storage: A beverage container 92 is placed on the base panel 102, where it is retained by the sidewalls 108 and the arc arms 122*a*, 122*b* of the upper holding bracket.

Once installed and loaded with items, the device 10 provides organized, accessible storage for the patient's essential items. The patient can reach any of the three items without assistance, reducing dependence on caregivers for basic needs and enhancing dignity and independence.

When bed adjustments are made (raising, lowering, or rotating the bed rails), the device 10 moves with the rail without interfering with the bed's motion. The attachment remains secure throughout normal bed operation. When the bed rail is lowered, the device fits in the space between the rail and mattress without causing interference or requiring removal, provided the bottle holder is in its stowed position.

When cleaning is required, the device 10 can be removed in seconds by simply lifting it off the bed rail. All surfaces can then be wiped down with hospital-grade disinfectant. The smooth, non-porous surfaces and minimized crevices enabled by the direct-mount compartment design enable thorough cleaning. The device is then reinstalled just as quickly.

When the patient is discharged, the device can be removed and either cleaned for the next patient or disposed of if single-patient use is preferred for infection control purposes. The low cost and simple construction make single-patient-use economically feasible if desired by the health-care facility.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. For example, additional compartments may be added for other items such as eyeglasses, tablets, remote controls for television, pens, notepads, or medical devices. The core three-compartment combination remains the primary inventive feature, but supplemental storage may enhance utility. Further, larger or smaller versions may be created for bariatric beds, pediatric beds, or non-hospital applications such as home care beds or nursing home beds. Still further, the device may include integrated electronics such as USB charging ports powered by a cord running to an electrical outlet, eliminating the need for separate phone chargers. Likewise, the device may include LED lighting in one or more compartments to illuminate contents for nighttime use. Still further, compartments may be vertically adjustable along the first inner face to accommodate different patient reach distances, and compartments may be color-coded, labeled, or include name plates for personalization in long-term care settings. Thus, it should be understood, therefore, that the invention may be practiced otherwise than as specifically set forth herein.

The invention claimed is:

1. A bedside attachment device for hospital beds, comprising:

a mounting system configured for tool-less attachment to a hospital bed rail without permanent mounting hardware, wherein the mounting system comprises an inverted U-shaped bracket having a first inner face and a second outer face spaced apart by a rail-receiving channel dimensioned to receive the hospital bed rail, wherein the first inner face has a height greater than a height of the second outer face such that the first inner face extends below a lower edge of the second outer face, and wherein the mounting system preserves full range of motion of the hospital bed rail;

three dedicated compartments mounted directly to the first inner face in fixed spatial relationship, the three dedicated compartments consisting of:

(i) a phone cradle compartment configured to receive a mobile phone and including a pass-through opening in a bottom portion thereof for routing a charging cable, (ii) a nurse-call handset slot compartment configured to receive a nurse-call handset, and (iii) a bottle holder compartment including a foldable bottle holder;

wherein the three dedicated compartments are sized such that when the bottle holder is in a stowed position, the device maintains a low profile enabling the device to fit between the hospital bed rail and a bed mattress when the hospital bed rail is lowered to a down position;

wherein the foldable bottle holder comprises:

a base panel pivotally mounted to the first inner face via first hinge brackets and first pivot pins, the base panel configured to rotate between a vertical stowed position against the first inner face and a horizontal deployed position extending perpendicular from the first inner face, and an upper holding bracket pivotally mounted to the first inner face via second hinge brackets and second pivot pins positioned above the first hinge brackets, the upper holding bracket comprising arc arms configured to extend around an upper portion of a beverage container when rotated from a vertical stowed position to a horizontal deployed position.

2. The device of claim 1, wherein the base panel includes three sidewalls extending upward from a perimeter edge thereof, the three sidewalls comprising a front sidewall and two side sidewalls, and wherein a rear edge of the base panel adjacent to the first inner face is free of sidewalls to enable pivoting motion to the vertical stowed position.

3. The device of claim 1, wherein the upper holding bracket is retained in the deployed position by a retention mechanism selected from the group consisting of: friction between the second pivot pins and pivot openings in the second hinge brackets, a detent mechanism, a snap-fit mechanism, and a magnetic retention mechanism.

4. The device of claim 1, wherein the mounting system, the three dedicated compartments, the first hinge brackets, and the second hinge brackets are integrally formed as a unitary molded structure from a medical-grade thermoplastic material comprising antibacterial additives.

5. The device of claim 1, wherein the phone cradle compartment comprises an outer wall, two side walls, a bottom wall, and an open top, wherein the phone cradle compartment is integrally molded with the first inner face.

6. A bedside attachment device for hospital beds, comprising:

a mounting system configured for tool-less attachment to a hospital bed rail without permanent mounting hardware, wherein the mounting system comprises a mounting bracket having a first inner face and a second outer face spaced apart to define a rail-receiving channel, wherein the first inner face has a height greater than a height of the second outer face, and wherein the mounting system preserves full range of motion of the hospital bed rail;

three compartments mounted directly to the first inner face in fixed spatial relationship, the three compartments comprising:

(i) a phone cradle compartment configured to receive a mobile phone and including a pass-through opening in a bottom portion of the phone cradle compartment for routing a charging cable, (ii) a nurse-call handset slot compartment configured to receive a nurse-call handset, and (iii) a bottle holder compartment including a beverage holder pivotally mounted to transition between a deployed position for holding a beverage container and a stowed position against the first inner face;

wherein the three compartments are sized such that when the beverage holder is in the stowed position, the device maintains a low profile enabling the device to fit between the hospital bed rail and a bed mattress when the hospital bed rail is lowered to a down position.

7. The device of claim 6, wherein the beverage holder comprises:

a base assembly including a base panel pivotally mounted to the first inner face via first hinge brackets to rotate between a vertical stowed position and a horizontal deployed position, and an upper holding bracket assembly including arc arms pivotally mounted to the first inner face via second hinge brackets positioned above the first hinge brackets, wherein the arc arms partially encircle a beverage container when in a deployed position.

8. The device of claim 6, wherein the nurse-call handset slot compartment comprises an outer wall, two side walls, a bottom wall, and an open top.

9. The device of claim 6, wherein the device is constructed from a material selected from the group consisting of: acrylonitrile butadiene styrene (ABS), polycarbonate (PC), and ABS/PC blends, and wherein the material includes antibacterial additives, and wherein all exterior surfaces comprise smooth, wipeable surfaces compatible with repeated cleaning using hospital-grade disinfectants.

10. The device of claim 6, wherein the mounting system enables universal mounting to either a left-side or right-side hospital bed rail with the first inner face facing toward a patient position in both configurations.

11. The device of claim 6, wherein at least one compartment of the three compartments is removably coupled to the first inner face at a selected one of a plurality of discrete attachment locations on the first inner face, enabling selective repositioning of the at least one compartment to accommodate user preferences regarding compartment arrangement.

12. The device of claim 11, wherein the at least one compartment is coupled to the first inner face via a removable attachment mechanism comprising at least one of: a sliding engagement with a dovetail track, a hook-and-slot mechanism, a snap-fit connection, or magnetic attachment elements.

13. The device of claim 11, wherein the plurality of discrete attachment locations are spaced vertically along the first inner face, and wherein the at least one compartment is selectively attachable at any of the plurality of discrete attachment locations to enable vertical repositioning of compartments based on user-preferred reach distance.

14. A bedside attachment device for hospital beds, comprising:

a mounting system configured for tool-less attachment to a hospital bed rail without permanent mounting hardware, the mounting system having a rail-receiving region that engages the hospital bed rail, and wherein the mounting system includes a retention feature configured to inhibit unintended removal of the device from the hospital bed rail during normal use while permitting intentional removal without tools;

at least three dedicated compartments supported by the mounting system, the at least three compartments comprising:

(i) a phone compartment configured to receive a mobile phone and including a cable-routing feature comprising at least one of an opening, a slot, a channel, a groove, or a guide for routing a charging cable to the mobile phone, (ii) a nurse-call handset compartment configured to receive a nurse-call handset, and (iii) a beverage holder configured to transition between a deployed position for holding a beverage container and a stowed position that minimizes a profile of the device.

15. The device of claim 14, wherein the beverage holder comprises a base panel pivotably mounted via first hinge brackets to rotate between a vertical stowed position and a horizontal deployed position.

16. The device of claim 15, wherein the beverage holder further comprises an upper holding bracket pivotably mounted via second hinge brackets positioned above the first hinge brackets, the upper holding bracket comprising arc arms configured to extend around an upper portion of a beverage container when in the deployed position.

17. The device of claim 14, wherein the mounting system comprises a first inner face and a second outer face, wherein the first inner face has a height greater than a height of the second outer face.

18. The device of claim 14, wherein at least one compartment is integrally molded with the mounting system as a unitary structure.

19. A method of organizing patient essential items at a hospital bedside, comprising:

providing a multi-compartment organizer having a mounting bracket with a first inner face and a second outer face defining a rail-receiving channel, and three dedicated storage compartments mounted to the first inner face for a mobile phone, a nurse-call handset, and a beverage container;

attaching the organizer to a hospital bed rail by positioning the mounting bracket over a top surface of the hospital bed rail with the rail-receiving channel aligned with the hospital bed rail, and lowering the organizer until interior surfaces of the first inner face and the second outer face engage opposite sides of the hospital bed rail, wherein the attachment is accomplished without tools or permanent hardware;

storing a mobile phone in a phone cradle compartment;

routing a charging cable through a pass-through opening in a bottom portion of the phone cradle compartment to a charging port of the mobile phone;

storing a nurse-call handset in a nurse-call handset slot compartment separate from the phone cradle compartment;

deploying a foldable bottle holder by rotating a base panel downward from a vertical stowed position against the first inner face to a horizontal deployed position extending perpendicular from the first inner face;

rotating an upper holding bracket downward from a vertical stowed position to a horizontal deployed position wherein arc arms of the upper holding bracket partially encircle an upper portion of a beverage container; and placing a beverage container on the base panel within the arc arms of the upper holding bracket.

20. The method of claim 19, further comprising:

stowing the foldable bottle holder by rotating the upper holding bracket downward to the vertical stowed position and rotating the base panel upward to the vertical stowed position, thereby reducing an overall depth profile of the organizer; and lowering the hospital bed rail to a down position while the organizer remains attached to the hospital bed rail, wherein the stowed bottle holder enables the organizer to fit in a space between the lowered hospital bed rail and a bed mattress without requiring removal of the organizer from the hospital bed rail.

\* \* \* \* \*